US006537589B1

(12) United States Patent
Chae et al.

(10) Patent No.: US 6,537,589 B1
(45) Date of Patent: Mar. 25, 2003

(54) CALCIUM PHOSPHATE ARTIFICIAL BONE AS OSTEOCONDUCTIVE AND BIODEGRADABLE BONE SUBSTITUTE MATERIAL

(75) Inventors: Soo Kyung Chae; Hong Yeoul Kim; Ho Yeon Lee; Chang Hun Lee; Kang Moon Seo, all of Seoul (KR)

(73) Assignee: Kyung Won Medical Co., Ltd., Seoul (KR)

( * ) Notice: Subject to any disclaimer, the term of this patent is extended or adjusted under 35 U.S.C. 154(b) by 0 days.

(21) Appl. No.: 09/624,794

(22) Filed: Jul. 25, 2000

(30) Foreign Application Priority Data

Apr. 3, 2000 (KR) .......................... 2000-17437

(51) Int. Cl.$^7$ .......................... A61K 33/42; A61K 9/00; A61K 33/04; A61K 33/06
(52) U.S. Cl. .................. 424/602; 424/422; 424/423; 424/426; 424/601; 424/606; 424/682; 424/696; 424/709; 424/722
(58) Field of Search ................ 424/422, 423, 424/426, 601, 602, 604, 606, 682, 696, 709, 722

(56) References Cited

U.S. PATENT DOCUMENTS 5,108,755 A  * 4/1992 Daniels et al. .............. 424/426

FOREIGN PATENT DOCUMENTS

| EP | 0 968 729 | * 1/2000 |
| WO | WO 97/45147 | * 12/1997 |

OTHER PUBLICATIONS

Special Report of Orthopedic Special Edition, Sep. 1999.

A Comparison of Magnetic Resonance and Computer Tomographic Image Quality After the Implantation of Tantalum and Titanium Spinal Instrumentation, By Jeffrey C. Wang, MD et al. Spine, vol. 23, No. 15, 1998.

* cited by examiner

Primary Examiner—Jose' G. Dees
Assistant Examiner—Frank Choi
(74) Attorney, Agent, or Firm—Bachman & LaPointe, P.C.

(57) ABSTRACT

An artificial bone promotive of osteoanagenesis comprising a calcium phosphate cement and a linear polyphosphate, wherein the calcium phosphate cement comprises β-tricalcium phosphate, monocalcium phosphate, calcium sulfate hemihydrate and other additives. The artificial bone is non-toxic to the body chemically stable, and has an excellent biodegradability. The artificial bone may be applied as substitutes for bone cements, allografts and autografts.

10 Claims, 14 Drawing Sheets

CALCIUM PHOSPHATE ARTIFICIAL BONE AS OSTEOCONDUCTIVE AND BIODEGRADABLE BONE SUBSTITUTE MATERIAL

FIELD OF THE INVENTION

The present invention relates to a novel calcium phosphate artificial bone as osteoconductive and osteoinductive, biodegradable substrate material which is highly able to promote biocompatible osteoanagenesis.

Particulary, the present invention relates to the novel calcium phosphate artificial bone promotive of biocompatible osteoanagenesis, which comprises an ordinary calcium phosphate bone cement and a linear polyphosphate comprising 3–200 orthophosphate molecules.

The polyphosphate-containing artificial bone of the present invention can substitute conventional bone cements, allografts and autografts which are used in the treatment of defects and fractures in every bone of the body, the cure of osteoporous, the fillers of implant for dental surgery, the bone substitute for plastic surgery, the substitution of defected bones in the operation on joints, including hip-joint, knee-joint and shoulder-joint, and the operation on the vertabra.

BACKGROUND

Bony tissues are connective tissues comprised of bone cells and extracellular matrices, but are different from other connective tissues in that the ossified connective substances within the extracellular matrices are inorganic. The inorganic substance consists mainly of calcium phosphate which exists as hydroxyapatite crystals($Ca_{10}(PO_4)(OH)_2$).

Bony tissues are hard enough to support and defend against physical stresses of the body, and their fracture or their density reduction or damage attributed to pathogenic changes may cause the body to suffer from deformity. When damaged or removed owing to any reasons, a bone has to be regenerated naturally or needs to be substituted with a prosthesis or a bone material from another body part by surgery. In addition, healing a physically broken(fractured) bone or a surgically damaged bone requires using various prosthetic tools, including artificial bones, for artificially relaying and immobilizing the bone. In this case, however, it takes a significantly long period of time for the bone to recover to its original figure and function while the patient suffers from serious physical and metal stresses. Further, as the healing procedure becomes long, the damaged part is increasingly apt to be under the danger of the infection with germs, so that a perfect curing effect may be not expected.

In the case of teeth, when an osseous tissue of maxillo-facial parts is fractured or damaged pathogenically or physically, its substitution or regeneration is important in many aspects.

Particularly, alveolar bones, which support teeth, are not only easily infected with bacteria, but also difficult to recover naturally to the original condition if they are infected with bacteria or broken by other factors. In one of the most prevalent treatment methods of compensating for a damaged bony tissue of a tooth, a titanium-based metal graft is inserted into the jaw bone to construct an artificial tooth. However, this graft method is disadvantageous in that the inserted graft exerts excessive occlusal on neighboring alveolar bones and the grafting surgical operation cannot be allowed if the bone supports around the site of interest are not sufficient.

There remains an urgent need to develop methods of facilitating the healing process(regeneration) of damaged bony tissues or inducing the morphogenesis of new bony tissues, or materials suitable for use in this purpose. In connection, there have been developed selective materials for bone increase and reconstruction, such as bioceramics, composite materials and bone derivatives, as well as artificial fillers for bone recovery, such as natural or synthetic polymers.

At present, demineralized bone, hydroxyapatite and other graft substitutes were developed and have been used to facilitate osteoanagenesis at damaged bony tissue parts, but do not bring about a satisfactory accomplishment in the regeneration of bony tissues, in practice. Recently, growth factors, such as bone morphogenic factors(BMF), platelet-derived growth factors(PDGF) and insulin-like growth factors(IGF), and cytokines have been reported to be very useful in the regeneration of bony tissues. Also, it has been reported that, in order for the growth factors and cytokines to act for the regeneration of bony tissues, it is most important to express their cellular receptors. When associated with the cellular receptors, the growth factors and cytokines trigger the normal wound healing of bony tissues. The mechanisms in which the growth factors and cytokines are involved in wound healing and tissue regeneration, however, have not yet been clearly revealed. Since the growth factors and cytokines are synthesized at trace amounts in different types of cells, recombinant techniques are required to produce the growth factors and cytokines at sufficient amounts for application for the wound healing of damaged bony tissues. However, the recombinant techniques are not broadly utilized on account of an economical reason of high production cost.

Besides induction of natural osteoanagenesis, substitution of damaged bony tissues is also being undertaken by facilitating osteogenesis with various bone onlays and bone graft substitutes. Application of bone onlays and bone graft substitutes is conducted largely by two methods: an autograft method and an allograft method. Both of the two methods utilize patients' own bones to induce osteogenesis. The bones to be grafted must be similar in elastic modulus to bones adjacent to the graft area because graft materials greatly different in elastic modulus, e.g., metal grafts generate excess stresses.

However, grafting methods utilizing bone onlays also suffer from several problems. When adopting an autograft method, the grafts to be available are quantitatively limited. In addition, while a surgical operation is conducted to extirpate a necessary bone for autograft, there always exist the dangers of bacterial infection and blood loss. In addition, the areas from which grafts are extirpated become poor in structural stability. The grafting technique, including the surgery operation, may force some patients to endure pain for a longer period of time than does fusion surgery. Over the autograft method, the allograft method has an advantage in that supply of allografts can be relatively achieved because they are obtained from allo-donors, but allogenic bones are far inferior in osteoinductive potential to autogenous bones and thus, can be used as only temporary supports.

Additional problems are also found in both the autograft and the allograft methods. For instance, since the grafts alone, used in the above graft methods, cannot offer stability large enough to endure the spinal marrow, an internal fixing method needs to be conducted concurrently. In this case, metal fixing means is used, requiring a more complicated surgical operation. In addition, the operator must repeatedly trim the graft into a precise size to fit into a targeted bony tissue, which results in extending the time it takes for the surgical operation. Further, in general, a smooth surface of a graft cannot provide a frictional force necessary for the graft to fix between adjacent bony tissues. Thus, the trimming always has the danger that the trimmed graft might slip out of the bony tissues, breaking the structure of the grafted bony tissue and causing damage to the nerve system and the vascular system near the bony tissue.

In order to circumvent these problems, active research has been directed to the development of bone graft substitutes which possess the excellent biomechanical properties of metal grafts and the superb biological properties of bone grafts, simultaneously as well as have not the disadvantages of the metal and bone grafts. As a result, various spinal marrow grafts which are comprised of hydroxyapatite and bovine collagen have been developed and are commercially available. In addition, such research has elicited the development of bioactive substitutes for cellular expression of the osteoanagenesis which is amplified in a cascade manner within cytoplasm, leading to the development of bone morphogenetic proteins usable as substitutes or sub-grafts as well as a series of osteoinductive factors synthesized from bone matrices, inductive of bone morphogenesis in grafted regions. Recombinant human bone morphogenetic protein-2(rhBMP-2) has been reported to be effective for the regeneration of damaged bones in various animal models. However, such proteins are also disadvantageous in that their use requires suitable carriers and fusion spacer tools.

In order to meet the necessity of safer and more convenient bone grafts, keen interest has recently been taken in bone graft substitutes, such as bioceramics. Calcium phosphate ceramics, one of the bioceramics, exhibit superior biocompatibility and are significantly freed from the bacterial infection and immunological danger which may be caused upon allograft. Therefore, with the advantages of allografting-bone grafts, calcium phosphate ceramics can be produced in abundance. In addition, such bioceramics are not only osteoconductive, but provide porous matrices which facilitate bone morphogenesis in bony tissues. However, bioceramics are disadvantageous in that internal fixation is required before grafting because their strength is too low to support the weight of the spinal marrow.

Bioceramics which are most prevalent include calcium phosphate, hydroxyapatite, and tricalcium phosphate. With superb biocompatibility, hydroxyapatite is chemically very similar to inorganic bone substances, but hard to degrade in vivo. In recent, the knowledge of hydroxyapatite's naturally occurring as a main building block in teeth and bones of some invertebrate animals brings about an intensive interest and significance in the compound and its modified forms. β-tricalcium phosphate is of fast biodegradability, but too weak to support heavy spinal marrows. Besides, numerous substances, including various forms of calcium phosphate, were designed to act as supports, substitutes, and controllers for bone morphogenesis or replacement.

Development was also achieved on various compositions of medical cements which can be applied in vivo. Of them, healing cements taking advantage of calcium phosphate possess excellent flexibility because tetracalcium phosphate, a main constituent of calcium phosphate, can be transformed into hydroxyapatite during the healing process. However, the time period that it takes for these healing cements to be cured makes it difficult to apply them in practice. Also, the healing cements find difficulty in being applied where body fluid is abundant because when cement is brought into contact with pseudo-body fluid immediately after being mixed(e.g., kneaded), the fluid may penetrate into and finally destroy the kneaded plaster. There are used two techniques to circumvent these problems. In one technique, the kneaded cement plaster paste is applied in vivo after being cured to some extent rather than immediately after being mixed. The other is to apply a kneaded cement paste only after the removing of body fluid and the completion of a hemostatic process. In both of the two methods, there are employed kneaded cement pastes which are cured to some degree and thus hard to handle. In addition, the methods are complicated and take a long period of time to be completed because of requiring body fluid removal, hemorrhage stopping, and additional processes.

In an effort to overcome these problems, an aqueous solution of an organic acid, such as citric acid or malic acid, or an inorganic acid, such as phosphoric acid, is applied for the kneading of such cement to reduce the time it takes to harden the kneaded cement paste. The kneaded cement paste prepared by use of such an acidic, aqueous solution, however, is so biostimulative as to cause inflammation in the applied body area. In order to prevent the breakdown of the cement, a chitosan-containing aqueous solution was suggested as a hardening solution for the cement. To dissolve chitosan, the aqueous solution has to be as low in pH as about 1–2, which is obtained by addition of an acid, and thus, the chitosan-containing hardening solution also can give rise to inflammation.

If damaged, various body joints, such as the total hip-joint, the total knee-joint and the total shoulder-joint, may be substituted by artificial bones.

Available for this purpose are synthetic materials which are prepared from a mixture of polymethylmetachlorite (PMMA) and benzoilperoxide. The artificial bones prepared from the synthetic materials, however, suffer from the serious problem of being not degraded naturally in vivo. Therefore, newly growing bones are obstructed by the persistent artificial bones, so that a high fever occurs, hurting the neighboring tissues. Conventionally, a patient suffering from a hernia of the cervial vspine, lumbar spine, or thoracic spine discs undergoes a surgical operation by use of autografts. To secure his or her own iliac bone, an additional operation must be performed on the patient, which forces him or her to suffer from additional pain and the patient may develop complications. Alternatively, bones taken from corpses, such as the fibula and ilium, are used as substitutes for use in the operation. This allografting operation certainly imposes a physically lighter burden on the patient, but suffers from many disadvantages of more feasible bacterial infection, poorer strength maintenance of grafts, higher material cost, and poorer biocompatibility. In addition, when allograft providers do not secure sufficient corpses, the supply and demand of allografts is not balanced.

Further, allografts find difficulty in keeping bone strength suitable for the patients who suffer from osteoporosis or who undergo an operation on ossa faciei or tops of the odontoid process. Upon allograft, a loosing is apt to happen.

Leading to the present invention, the intensive and thorough research on an ideal osteoregenerative, bone substitute material, repeated by the present inventors, resulted in the finding that a mixture of calcium phosphate cement and polyphosphate meets requirements for use in bone grafting, including biocompatibility, sterilization, osteoinductivity, osteoconductivity, biodegradability, with freedom from immunogenicity and toxicity to tissues and is suitable for use in osteoanagenesis and bone morphogenesis.

Polyphosphate is a linear polymer consisting of tens to hundreds of orthophosphate residues(Pi) which link to each other via high-energy phosphoanhydride bonds. Polyphosphate accumulating bacteria possess polyphosphate from which orthophosphate is successively released to provide energy just like ATP in the body. Under stress such as undernutrition, heat or an osmotic pressure change, polyphosphate accumulating bacteria actively synthesize polyphosphates for their survival. In other words, polyphosphate acts as a regulator for such an external stress. Recently, polyphosphate has been found to be of antibacterial activity. In addition, polyphosphate is reported to have characteristic functions, including contribution to the association of water and flesh, improvement in assimilation processes, and retardation of oxidative odorizing and discoloration.

Taking advantage of the functional characteristics of polyphosphate, the present invention supplements polyphosphate to conventional artificial bone materials to prepare novel bone substitutes undoubtedly superior in bone morphogenesis without causing side effects.

Therefore, it is an object of the present invention to overcome the foregoing and the other disadvantages encountered in prior arts and to provide a novel polyphosphate-containing calcium phosphate artificial bone as osteoconductive and osteoinductive, biodegradable substitute material which is highly able to promote biocompatible osteoanagenesis.

The polyphosphate-containing artificial bone supplemented with polyphosphate of the present invention can substitute conventional artificial bones which are substituted for joints, such as total hip joints, total knee joints, total shoulder joints, and other joints, by surgical operations, without side effects the conventional ones cause. In addition, upon operations on the cervical spine, the thoracic spine, and the lumbar spine, the polyphosphate-containing artificial bone of the present invention is also used as a filler where a tissue slice to be grafted has a cage shape. Therefore, the polyphosphate-containing artificial bone of the present invention is a biocompatible, osteoanagenetic, bone substitute material which is useful as a filler, a reinforcement and a support for vertebra plasty and oral graft operation.

SUMMARY OF THE INVENTION

It is an object of this invention to provide a novel calcium phosphate artificial bone as osteoconductive and osteoinductive, biodegradable substrate material which is highly able to promote biocompatible osteoanagenesis.

In accordance with the present invention, the foregoing objects and advantages are readily obtained.

The present invention provides the calcium phosphate artificial bone material promotive of biocompatible osteoanagenesis, which comprises an ordinary calcium phosphate bone cement and a linear polyphosphate comprising 3–200 orthophosphate molecules.

Further features of the present invention will appear hereinafter.

DETAILED DESCRIPTION OF PREFERRED EMBODIMENTS

Figure 1:
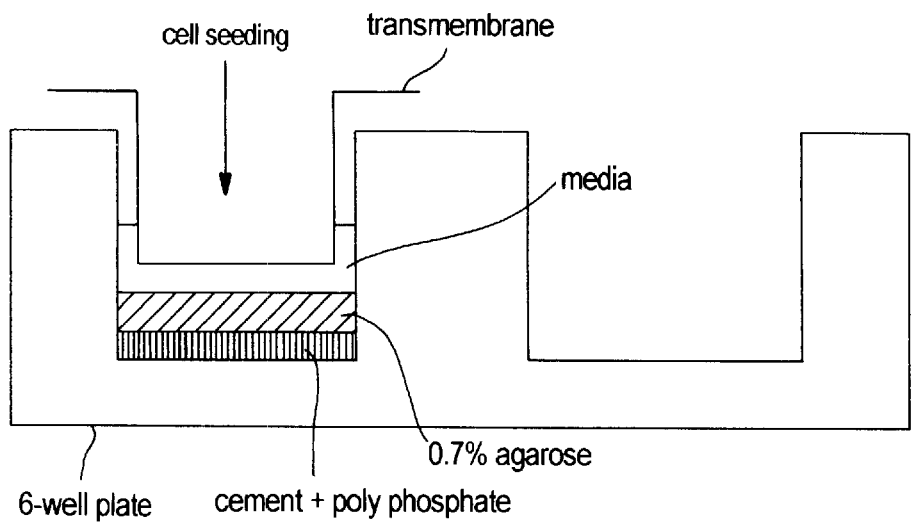
FIG. 1 shows a schematic cross section illustrating a cell culture process by use of a transmembrane.

Hereinafter, the present invention is described in detail.

The present invention provides a novel calcium phosphate artificial bone substitute promotive of biocompatible osteoanagenesis having osteoconductive and osteoinductive activities, prepared from calcium phosphate cement and linear polyphosphate.

The biocompatible, osteoanagenetic calcium phosphate is evaluated as an ideal substitute or filler for damaged bones. Examples of such calcium phosphate include dicalcium phosphate dehydrate(DCPD), dicalcium phosphate(DCP), tetracalcium phosphate(TTCP), and hydroxyapatite(HA).

The calcium phosphate cement constituting the calcium phosphate artificial bone substitute of the present invention may be one well known in the art, mainly comprising β-tricalcium phosphate, monocalcium phosphate, and/or calcium sulfate hemihydrate, but is not limited thereto. It should be noted that modification in part or all of the components is possible and within the scope of the invention.

Preferably, the calcium phosphate cement is prepared from a mixture composed, by weight, of 40–58% of β-tricalcium phosphate, 10–15% of monocalcium phosphate, 8–12% of calcium sulfate hemihydrate, and 5–20% of other additives. For preparation of the calcium phosphate cement, the mixture is sterilized by autoclaving, and solidified firmly. When the growth conditions for osteoblast is taken account of, the calcium phosphate cement is preferably maintained to pH range from 7.0 to 7.4 upon the solidification.

The present invention provides a novel artificial bone cement by supplementing polyphosphate superior to conventional ones in the requirements osteoanagenetic, artificial bone substitutes.

Polyphosphate, a simple structure formed by a multitude of phosphodiester bonds, has a function of promoting bone regeneration in combination with conventional artificial bone cement. Especially, polyphosphate salts, such as potassium polyphosphate and sodium polyphosphate, are preventive of the degradation of vitamin C and the discoloration of natural pigments and synthetic dyes as well as the deodorant of metal ions. When being associated with polyphosphate, proteins or peptides can be solubilized in water. Thus, polyphosphate brings about an improvement in the hydration and water retention of proteins or peptides. Further, polyphosphate is so safe to the body that it is approved as a food additive. In fact, polyphosphate is applied to protein foods with the aim of softening the foods by taking advantage of polyphosphate's function of aiding water to penetrate into proteins or peptides.

In the case of being mixed in a liquid phase, the polyphosphate of the present invention is preferably provided as a salt form, but not limited thereto. If existing as a linear structure, there may be used any type of polyphosphate associated with metals or chemicals. Preferable are sodium salts, potassium salts and calcium salts.

Polyphosphate which can be added to the artificial bone cement of the present invention is not particularly limited in configuration, but preferably has a linear structure. Based on the total weight of the artificial bone cement, polyphosphate is preferably used at an amount of 0.001 to 0.05 % by weight. For example, if the artificial bone cement has a polyphosphate content of less than 0.001% by weight, desired effects cannot be obtained. On the other hand, if the polyphosphate content exceeds 0.05% by weight, the osteoblast undergoes cell death.

Another parameter determining the osteoanagenetic effect of the artificial bone cement is the chain length of polyphosphate. Selecting an appropriate chain length of polyphosphate conduces to improving the osteoanagenic potential of the artificial bone cement because the chain length of polyphosphate has influence on the transcription rate of osteocalcin, an important gene product of osteoblast. In regard to the chain length, polyphosphate preferably ranges, in orthophosphate residue number, from 3 to 200, more preferably from 10 to 100, and most preferably from 60 to 80.

The polyphosphate-containing artificial bone cement of the present invention is involved in osteoanagenesis by activating the transcription of an osteoblast-forming gene. This function can be verified from in vitro tests using MG-63 and HOS-TE85 cells, both being osteoblast strains, and in vivo tests using beagle dogs(see FIGS. 7 to 10).

The polyphosphate-containing artificial bone with the advantages of being non-toxic to the body, chemically stable and biodegradable of the present invention is useful for the treatment of fractured bones or bone defective areas and can substitute the conventional artificial bones, allografts, and autografts which are used in total joint substitution and vertebra operation.

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Preparation of Artificial Bone Material Containing Polyphosphate 5.47 g of β-tricalcium phosphate, 1.33 g of monocalcium phosphate, and 1.07 g of calcium sulfate hemihydrate were homogeneously mixed. From the main calcium phosphate mixture, 0.16 g was taken and, then, autoclaved at 121° C. under a pressure of 15 psi while being wrapped up in aluminum foil. After completion of the autoclaving, the mixture was poured in a sterilized six-well plate or a 100 mm culture dish and solidified. In order to keep the mixture at 7.0–7.4 in pH during the solidification, 100 ul of 0.15 N NaOH and 200 ul of sterilized, deionized water were thinly spread over the well plate or dish, followed by drying the well plate or dish for 2–3 hours in an incubator maintained at 37° C.

In order to add sodium polyphosphate into the prepared calcium phosphate cement, each of sodium polyphosphates solutions having 5, 15, 25, 35, 45, 65 and 75 chain length were diluted into a 0.05 wt %, a 0.01 wt % and a 0.005 wt % solution by using a 10% stock solution, respectively, which were then mixed with the calcium phosphate cement. Solidification of these mixtures afforded artificial bone materials of the present invention.

Experimental Example 1

In vitro Tests for Determining Toxicity Buffering Effects of Calcium Phosphate on Cells <1-1> Cell Culture Human osteoblast strains MG-63(male, osteosarcoma, Korean Cell Line Bank, Cat. #21247) and HOS-TE85 (female, osteosarcoma, Korean Cell Line Bank, Cat. #21543) were used for in vivo tests for determining toxicity buffering effects of calcium phosphate.

Particulary, human osteoblast strains MG-63 and HOS-TE85 were seeded in 100 mm culture dishes or T-75 culture flasks. While MG-63 was cultures in an MEM(minimum essential medium) contained in the dishes or flasks for culturing MG-63, HOS-TE85 was cultured in a DMEM (Dulbeco's modified Eagle medium) containing 3.7 g/L of sodium bicarbonate and 2.5 g/L of HEPES buffer. Each culture medium was supplemented with 2 mM L-glutamine, 0.1 mM non-essential amino acids, 1.0 mM sodium pyruvate, 10% fetal bovine serum(FBS), and 1% penicillin-streptomycin(10,000 U/ml). The culture media were substituted with fresh ones twice a week.

The osteoblast cells were sub-cultured once or twice a week in an incubator which was maintained at 37° C. in an atmosphere comprising 5% CO2 and 95% O2. Before use, FBS was pre-heated at 56° C. for 30 min. All of the reagents used in this cell culture were purchased from Gibco. BRL Co., USA.

<1-2> Cell Culture Using Artificial Bone Cement-Containing Media

Using the polyphosphate-containing artificial bone cement prepared in Example 1, human osteoblast cells MG-63 and HOS-TE85 were cultured in the following two manners.

<1-2-1> Transmembrane Application

Over the polyphosphate-containing artificial bone cement of the present invention which had been solidified on a 6-well plate, 2–3 ml of the cell culture medium was added to completely cover the bone cement, as shown in FIG. 1. A sterile transmembrane, a kind of collagen coated polytetrafluorethylene membrane(Transwell-COL, Coster USA) was put on the culture medium, after which cells were seeded on the transmembrane and cultured.

<1-2-2> Agarose Application

Figure 2:
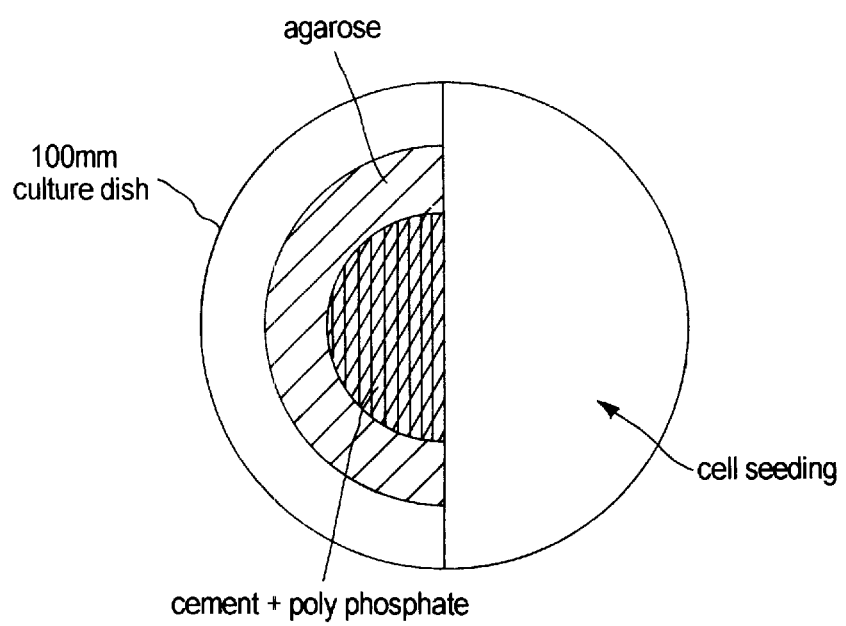
FIG. 2 shows a schematic plan view illustrating a cell culture process by use of agarose.

A 0.7% solution of agarose(low melting point agarose, Sigma USA) in sterile deionized water was maintained at an appropriate temperature. Over the polyphosphate-containing artificial bone material of the present invention which had been solidified on a 100 mm culture dish, 3 ml of the 0.7% agarose solution was so slowly added by use of a 1000 ml pipette as not to collapse the solidified artificial bone to the complete covering of the artificial bone. The agarose solution was poured over only the polyphosphate-containing artificial bone material prepared in Example 1 and solidified. Upon the solidification of the polyphosphate-containing artificial bone material on the 100 mm culture dish, the artificial bone material was rendered to occupy only a half of the culture dish area in order that the other half area would be provided for seeding cells, as shown in FIG. 2.

<1-3> Cell Seeding and RNA Isolation

MG-63 and HOS-TE85 cells cultured in Experimental Example <1-2> were harvested from respective culture dishes and dissolved in sterilized, deionized water. 20 ul of each cell solution was dyed with 0.4% tryphan blue and the number of cells was counted with the aid of a hemocytometer. Artificial bone materials which contained type 65 and type 75 polyphosphate, respectively, were solidified on culture dishes or 6-well plates, provided as matrices on which cells were seeded at a density of $1.0 \times 10^4$ cells/ml, and attached onto culture dishes.

To attach the test cells onto culture dishes, calcium-free EMEM(BioWhittaker, Walkersville, Md.) added with 1 M HEPES buffer(60 ml/L), 10% FBS, and 1% penicillin-streptomycin, was used and refreshed every three days.

After 72 hours of culturing, total RNAs were extracted from each of MG-63 and HOS-TE85 cells. 1 ml of Trizol (Gibco BRL) was poured in each culture dish and cells were harvested by use of a scraper. The cell harvest was homogenized in 1.5 ml microtubes with the aid of 18–21 G syringes and centrifuged at 4° C. at 12,000 rpm for 10 min. The supernatant, after being added with 200 ul of a mixture of 25:24:1 phenol:chloroform:isoamylalcohol, was allowed to stand for 5–15 min at room temperature to give a clear layer which was, then, centrifuged at 4° C. at 12,000 rpm for 15 min. In a new microtube, the RNA layer thus obtained was mixed with one volume of absolute isopropyl alcohol, allowed to stand for 5–15 min at room temperature and centrifuged at 4° C. at 12,000 rpm for 5 min. The RNA pellet was thoroughly dried at room temperature for 5–10 min, added with 100 ul of DEPC water, and quantitatively measured by a UV spectrometer(Hewlett Packard USA).

<1-4> Reverse-Transcriptase Polymerase Chain Reaction (RT-PCR)

From the RNA obtained in Experimental Example <1-3>, a cDNA was synthesized by thermally treating at 42° C. for 30 min and then, 75° C. for 30 min and used as a template for a PCR. In this regard, a human glyceraldehydes 3-phosphate dehydrogenase(GAPDH) gene, a kind of a house-keeping gene, was used as a positive control. Using a set of the sense primer GAPDN-N represented by Seq. ID No. 3 and the antisense primer GAPDH-C represented by Seq. ID No. 4, a PCR for the control started with 95° C. pre-denaturation for 3 min and carried out with 30 cycles of denaturing temperature at 95° C. for 30 sec, annealing temperature at 63° C. for 30 sec and extending temperature at 72° C. for 30 sec, finally followed by 72° C. extension for an additional 7 min. For amplification of an osteocalcin gene, a PCR using a set of the sense primer OCN-sense represented by Seq. ID No. 1 and the antisense primer OCN-antisense represented by Seq. ID No. 2 started with 95° C. pre-denaturation for 3 min and carried out with 30 cycles of denaturing temperature at 95° C. for 30 sec, annealing temperature at 55° C. for 30 sec and extending temperature at 72° C. for 30 sec, finally followed by 72° C. extension for an additional 7 min. Mixture compositions for the RT-PCR and the PCR are given in Table 1, below.

TABLE 1

Mixture compositions for the RT-PCR and the PCR

| cDNA synthesis (RT PCR) mixture | | PCR mixture | |
|---|---|---|---|
| 5 × RT buffer | 6 ul | 5 × RT buffer | 2.5 ul |
| 10 mM NTP | 0.5 ul | 10 mM NTP | 0.5 ul |
| random primers | 1 ul | sense primer (10 p) | 1.0 ul |

TABLE 1-continued

Mixture compositions for the RT-PCR and the PCR

| cDNA synthesis (RT PCR) mixture | | PCR mixture | |
|---|---|---|---|
| 100 mM DTT | 1 ul | anti-sense primer (10 p) | 0.3 ul |
| MMLV reverse transcriptase | 1 ul | Taq polymerase (5 U) | 0.3 ul |
| RNase | 9.1 ul | RT mixture | 1.0 ul |
| RNA template | 1 ul | DEOC water | 18.7 ul |
| DEPC water | 9.4 ul | | |
| total | 30 ul | Total | 25 ul |

<1-5> Agarose Gel Electrophoresis 10 ul of the RT-PCR product obtained in Experimental Example <1-4> was analyzed by electrophoresis on 1.5% agarose gel. The electrophoresis was conducted for 40 min at 100 V using 1×TAE(Tris-acetate) buffer. After completion of the electrophoresis, the agarose gel was dyed in EtBr (ethidium bromide) for 20 min and decolored in deionized water for 15–20 min. The decolored gel was observed on a UV transilluminator(Paramount), examined again by use of a photodoc system(GEL-DOC, Bio-Rad, USA), and photographed.

Experimental Example 2

Effect of Polyphosphate Artificial Bone on Description of Osteoblast Forming Gene <2-1> Determination on Transcription Rate of Osteoblast Forming Gene of MG-63

All experiments were carried out in the same manners as in Experimental Example 1. After being inoculated into artificial bones mixed with both types 65 and 75 polyphosphate of 0.005 wt %, 0.05 wt % and 0.01 wt %, respectively, MG-63 cells were cultured for 72 hours and subjected to RNA isolation. As a control, there were used MG-63 cells which had been grown alone.

A set of osteoblast forming gene-specific primers, as represented by Seq. ID Nos. 1 and 2, were applied for RT-PCR using the isolated RNAs as respective templates.

Figure 3:
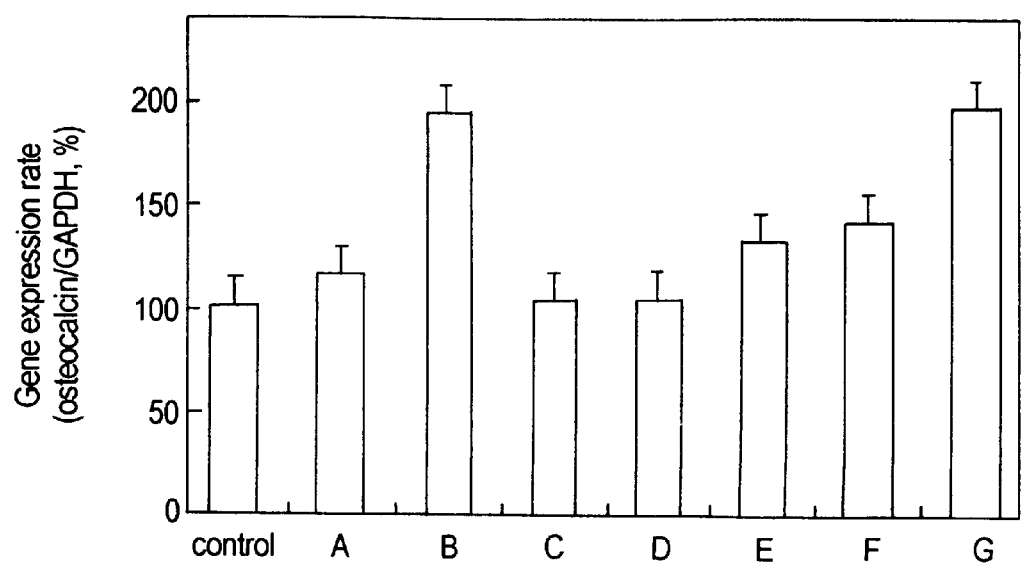
FIG. 3 shows a histogram illustrating the effects of the polyphosphate-containing artificial bones of the present invention on the transcription of an osteoblast-forming gene of MG-63 cells, where Control; when the cells cultured alone,
A; on a conventional bone cement,
B; on a conventional bone cement supplemented with 0.005 wt % type 75 polyphosphate,
C; on a conventional bone cement supplemented with 0.01 wt % type 75 polyphosphate,
D; on a conventional bone cement supplemented with 0.05 wt % type 75 polyphosphate,
E; on a conventional bone cement supplemented with 0.005 wt % type 65 polyphosphate,
F; on a conventional bone cement supplemented with 0.01 wt % type 65 polyphosphate, and
G; on a bone cement supplemented with 0.05 wt % type 65 polyphosphate.
Figure 5:
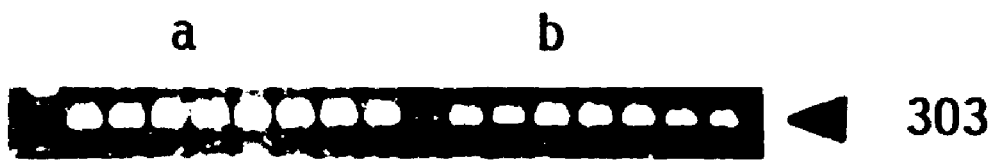
FIG. 5a shows an electrophoresis result of RT-PCR products from Hos-TE85 cells, where Lane 1; a DNA marker(DNA ladder),
Lane2; a control,
Lane 3; an RT-PCR product from Hos-TE85 cells grown on a cement only,
Lane 4; an RT-PCR product from cells grown on cement+ 0.005 wt % type 75 polyphosphate,
Lane 5; an RT-PCR product from cells grown on cement+ 0.01 wt % type 75 polyphosphate,
Lane 6; an RT-PCR product from cells grown on cement+ 0.05 wt % type 75 polyphosphate,
Lane 7; an RT-PCR product from cells grown on cement+ 0.005 wt % type 65 polyphosphate,
Lane 8; an RT-PCR product from cells grown on cement+ 0.01 wt % type 65 polyphosphate, and
Lane 9; an RT-PCR product from cells grown on cement+ 0.05 wt % type 65 polyphosphate.
FIG. 5b shows an electrophoresis result of RT-PCR products from MG-63 cells, where Lane 10; a control,
Lane 11; an RT-PCR product from MG-63 cells grown on a cement only,
Lane 12; an RT-PCR product from cells grown on cement+0.005 wt % type 75 polyphosphate,
Lane 13; an RT-PCR product from cells grown on cement+0.01 wt % type 75 polyphosphate,
Lane 14; an RT-PCR product from cells grown on cement+0.05 wt % type 75 polyphosphate,
Lane 15; an RT-PCR product from cells grown on cement+0.005 wt % type 65 polyphosphate, Lane 16; an RT-PCR product from cells grown on cement+0.01 wt % type 65 polyphosphate, and Lane 17; an RT-PCR product from cells grown on cement+0.05 wt % type 65 polyphosphate.
Figure 6:
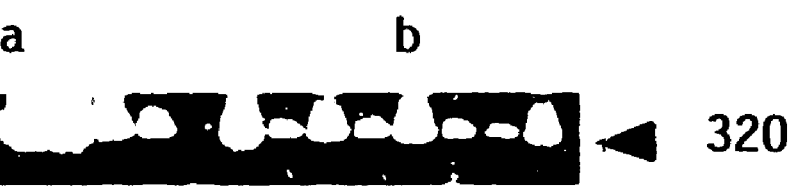
FIG. 6a shows an electrophoresis result of GAPDH RT-PCR products from Hos-TE85 cells, where Lane 1; a DNA marker(DNA ladder), Lane 2; a control, Lane 3; an RT-PCR product from Hos-TE85 cells grown on a cement only, Lane 4; an RT-PCR product from cells grown on cement+ 0.005 wt % type 75 polyphosphate, Lane 5; an RT-PCR product from cells grown on cement+ 0.01 wt % type 75 polyphosphate, Lane 6; an RT-PCR product from cells grown on cement+ 0.05 wt % type 75 polyphosphate, Lane 7; an RT-PCR product from cells grown on cement+ 0.005 wt % type 65 polyphosphate, Lane 8; an RT-PCR product from cells grown on cement+ 0.01 wt % type 65 polyphosphate, and Lane 9; an RT-PCR product from cells grown on cement+ 0.05 wt % type 65 polyphosphate.
FIG. 6b shows an electrophoresis result of osteocalcin RT-PCR products from MG-63 cells, where Lane 10; a control, Lane 11; an RT-PCR product from MG-63 cells grown on a cement only, Lane 12; an RT-PCR product from cells grown on cement+0.005 wt % type 75 polyphosphate, Lane 13; an RT-PCR product from cells grown on cement+0.01 wt % type 75 polyphosphate, Lane 14; an RT-PCR product from cells grown on cement+0.05 wt % type 75 polyphosphate, Lane 15; an RT-PCR product from cells crown on cement+0.005 wt % type 65 polyphosphate, Lane 16; an RT-PCR product from cells grown on cement+0.01 wt % type 65 polyphosphate, and Lane 17; an RT-PCR product from cells grown on cement+0.05 wt % type 65 polyphosphate in lane 17.
Figure 7A:
FIG. 7 shows histochemical examination results of a thighbone specimen of a beagle dog, where 7A shows a gross appearance which is not treated after a defect is caused in its thighbone, 7B is a cross section of 7A, 7C is a picture through an optical microscope with a nine times magnification of 7B, 7D is a picture through an optical microscope with a 40 times magnification of 7C, and 7E is a picture through an optical microscope with a hundred times magnification of 7D.
Figure 7B:
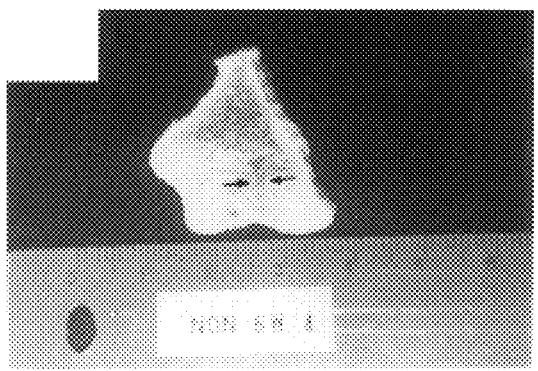
Figure 7C:
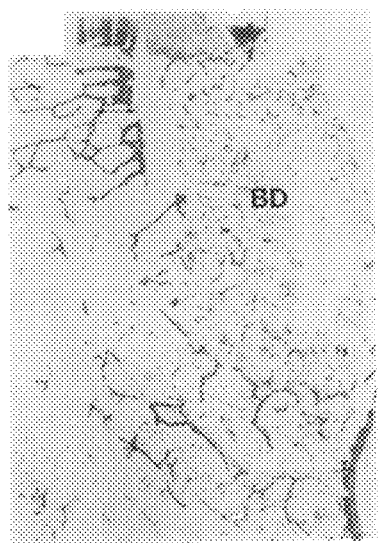
Figure 7D:
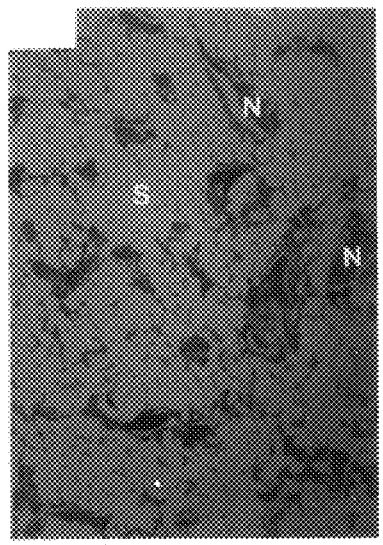
Figure 7E:
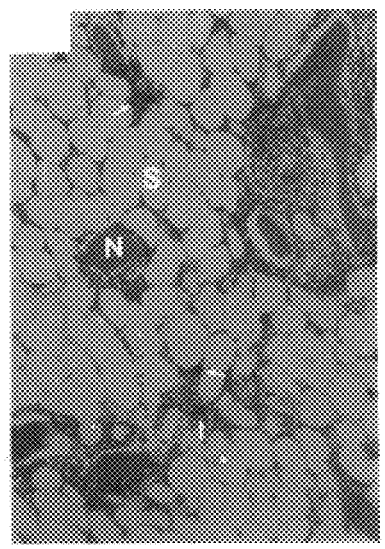

Gel band densities appearing upon the electrophoresis of the above RT-PCR products were compared with those appearing upon the electrophoresis of the RT-PCR products obtained by use of GAPDH-specific primers(FIGS. 3, 5b and 6b).

In general, the cells added with the polyphosphate-containing artificial bone materials of the present invention were two- or three-folds higher in transcription rate than the cells added with conventional artificial bones. Especially, the cells added with artificial bone materials comprising a conventional artificial bone cement in combination with 0.005 wt % of type 75 polyphosphate and 0.05 wt % of type 65 polyphosphate were found to be remarkably improved in the transcription rate of the osteoblast forming gene. These results indicate that the polyphosphate added in the conventional artificial bone cement gives a contribution to the a rapid bone morphogenetic effect by increasing the activity of osteoblast.

<2-2> Determination on Transcription Rate of Osteoblast Forming Gene of HOS-TE85

All experiments were carried out in similar manners to those for the above MG-63 cells.

Figure 4:
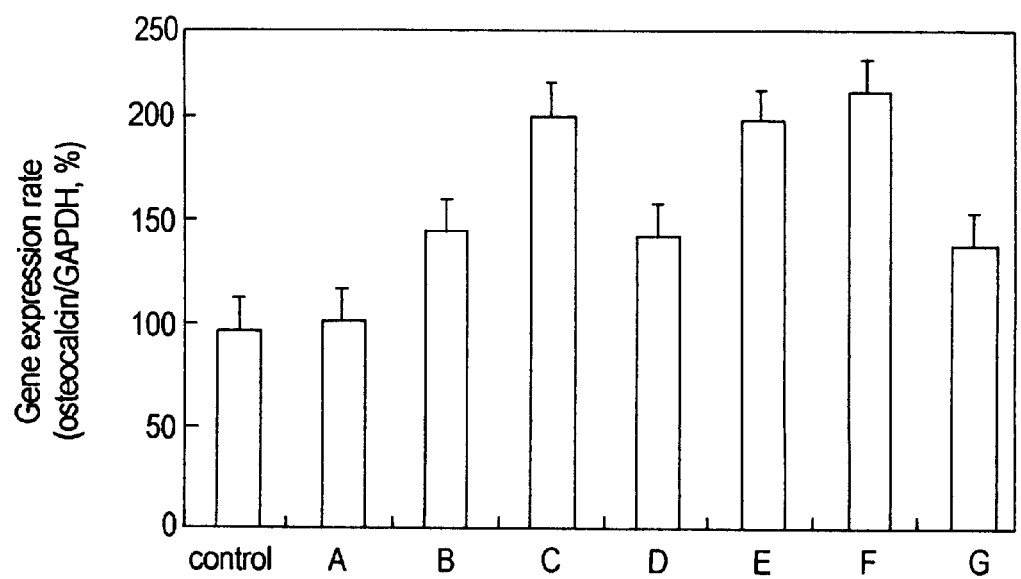
FIG. 4 shows a histogram illustrating the effects of the polyphosphate-containing artificial bones of the present invention on the transcription of an osteoblast-forming gene of Hos-TE85 cells, where Control; when the cells are cultured alone,
A; on a conventional bone cement,
B; on a conventional bone cement supplemented with 0.005 wt % type 75 polyphosphate,
C; on a conventional bone cement supplemented with 0.01 wt % type 75 polyphosphate,
D; on a conventional bone cement supplemented with 0.05 wt % type 75 polyphosphate,
E; on a conventional bone cement supplemented with 0.005 wt % type 65 polyphosphate,
F; on a conventional bone cement supplemented with 0.01 wt % type 65 polyphosphate, and
G; on a bone cement supplemented with 0.05 wt % type 65 polyphosphate.

Both HOS-TE85 cells added with artificial bones comprising 0.005 wt % of type 75 polyphosphate and 0.05 wt % of type 65 polyphosphate were about twice as high in the transcription rates of osteoblast forming genes as a control. The cells added with artificial bones comprising 0.005 wt % and 0.01 wt % of type 65 polyphosphate showed the transcription rate of the osteoblast forming gene about 1.5-folds higher than that of the control (FIGS. 4, 5a and 6a). Although somewhat different in the transcription rate from MG-63 of Experimental Example <2-1> depending on the chain length of polyphosphate, HOS-TE85 cells were generally superior in osteoblast forming activity to the control.

Experimental Example 3

In vivo Tests for Determining Osteoanagenesis Promoting Effect of Polyphosphate-containing Artificial Bone Material In order to examine the osteoanagenesis promoting effect of polyphosphate-containing artificial bone of the present invention, these inventors inserted the polyphosphate-containing artificial bone in bone defects, which were caused in condylar thighbones of beagle dogs by surgical operation, and examined its osteoanagenesis promoting effects.

<3-1> Experimental Animals

Bone defects were introduced to left and right thighbones of two male beagle dogs, each being one year old or older with a body weight of about 15 kg.

In order to exclude the osteoanagenesis attributed to the bone growth plate and estrogen, the experimental animals must be one-year old or older and male. At least one week before the surgical experiment, the experimental animals were confined into the experimental room and administered with anthelmintic medicines and subjected to a vaccination. Experiments were not started until they were recognized to adapt themselves to the new circumstance. One of the two experimental groups was treated with the artificial bone containing 0.01 wt % of type 65 polyphosphate of the present invention while the other was treated with the artificial bone containing no polyphosphates.

<3-2> Preparation of Artificial Bones

An artificial bone material containing 0.01 wt % of type 65 polyphosphate was prepared according to the method of Example 1. The artificial bone material was molded into a cylindrical block which was 10 mm long with a diameter of 4.8 mm. In regard to the molding, the artificial bone cement material was poured in a stainless cylinder with an inner diameter of 4.8 mm before being solidified. A surgical operation was conducted to cause a bone defect.

<3-3> Treatment of Experimental Animal Groups

Preoperative preparation for experimental animals was executed according to general indications.

By injection with atropine at a dose of 0.05 mg/kg and then muscular injection with ketamine at a dose of 15 mg/kg and xylazine at a dose of 2 mg/kg, the experimental animals were allowed to be under general anesthesia.

The polyphosphate-containing artificial bone material of the present invention was inserted into one of the left and the right thighbones of the thoroughly anesthetized animals while a conventional artificial bone material, lacking polyphosphate, was inserted into the other of the left and the right thighbones. For this, a hole 10 mm deep was formed in a predetermined site of an exposed thighbone region with the aid of a 3.5 mm drill tip and then widened with the aid of a 5 mm drill tip. To this bone defective site, the artificial bone cement block prepared in Experimental Example <3-2> was inserted, after which the soft tissues and epidermis were closed according to general operative manners.

After the operation, the animals were injected for three days with sefazolin to prevent bacterial infection. The operated regions were protected with bandaging while Elizabeth's collars were put on around their necks for the animals not to disturb the bandaged sites.

<3-4> Histological Examination

On the sixth week after the surgical operation, all of the experimental animals were subjected to mercy killing, followed by taking thighbone samples therefrom. After being transversely cut using a precise saw, the bone samples were immersed for 46 hours in 10% buffered formalin(pH 7.6) for fixation. The fixed samples were decalcified by use of a decalcification agent(Plank-Rychlo solution), immersed in a 5% $Na_2SO_4$ solution, and fixed in a 10% formalin solution. The samples were allowed to undergo a tissue processing procedure to produce paraffin embeddings which were then cut into slices five um thick. Dyeing the slices with hematoxylin-eosin(H&E) facilitated the observation under an optical microscope.

The optical microscope results are shown in FIG. 7. A tissue specimen of the beagle dog thighbone distal extrerrity, in which the artificially caused bone defective region was treated with no measures, showed that sinusoids(S) were significantly formed around the bone defect(BD) with a partial formation of a new bone(N). However, osteoclast (indicated by an arrow) still prevailed in the defect.

Figure 8A:
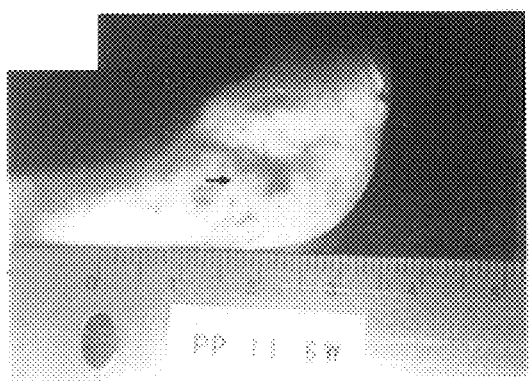
FIG. 8 shows histochemical examination results of a thighbone specimen of a beagle dog, into which an artificial bone containing 0.01 wt % type 65 polyphosphate is introduced after a defect is caused in its thighbone, where 8A is a gross appearance, 8B is a cross section of 8A, 8C is a picture through an optical microscope with a nine times magnification of 8B, 8D is a picture through an optical microscope with a 40 times magnification of 8C, and 8E is a picture through an optical microscope with a hundred times magnification of 8D.
Figure 8B:
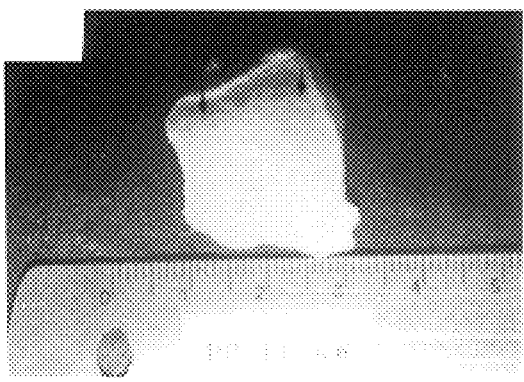
Figure 8C:
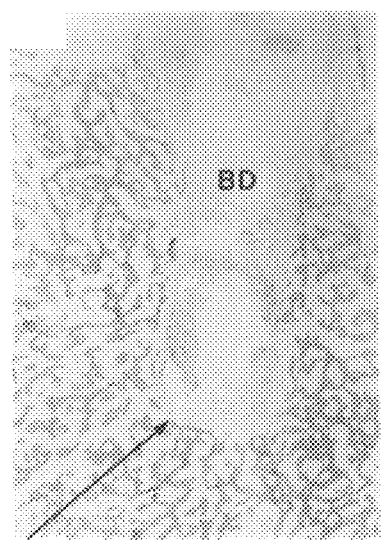
Figure 8D:
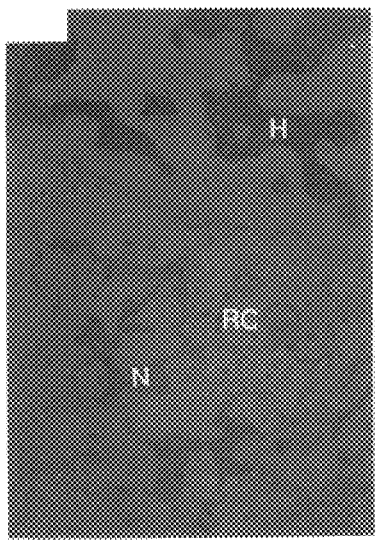
Figure 8E:
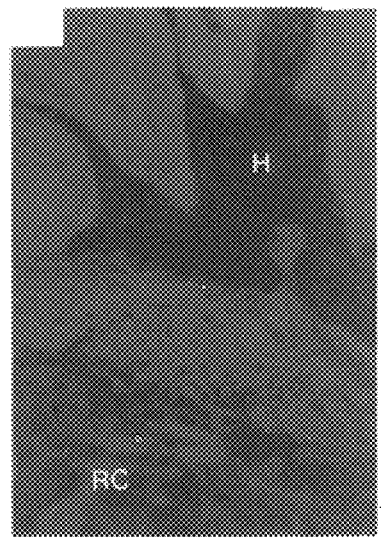

In contrast, a tissue specimen of the beagle dog thighbone distal extrerrity, in which the artificial bone cement containing 0.01 wt % of type 65 polyphosphate was transplanted into the artificially caused bone defective region, showed that a new bone (N) grew into the bone cement(BC). In addition, densely grown osteoblast(indicated by an arrow) was found around the new bone and the bone cement, indicating the occurrence of active osteoanagenesis, as shown in FIGS. 8c and 8d. In the 100 times magnified, optical microscopic photograph of FIG. 8e, osteoblast can be further clearly seen which was densely grown around the bone cement and new bone while the new bone grew surrounding the bone cement.

Observation of a cross section of the thighbone into which the artificial bone was transplanted provided the knowledge that almost all of the marrow around the bone cement was substituted by the white matrix.

Figure 9A:
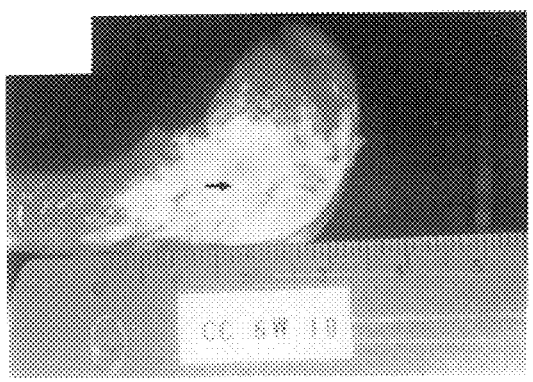
FIG. 9 shows histochemical examination results of a thighbone specimen of a beagle dog, into which an artificial bone containing no polyphosphate is introduced after a defect is caused in its thighbone, where 9A is a gross appearance, 9B is a cross section of 9A, 9C is a picture through an optical microscope with a nine times magnification of 9B, 9D is a picture through an optical microscope with a 40 times magnification of 9C, and 9E is a picture through an optical microscope with a hundred times magnification of 9D.
Figure 9B:
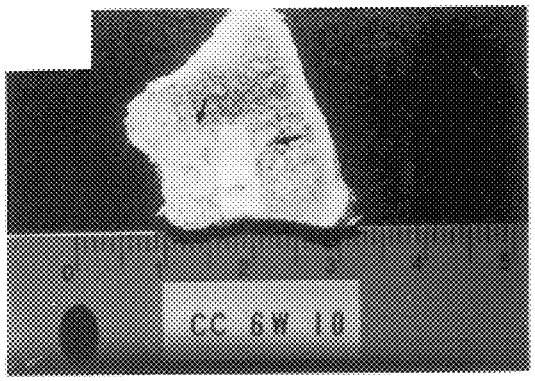
Figure 9C:
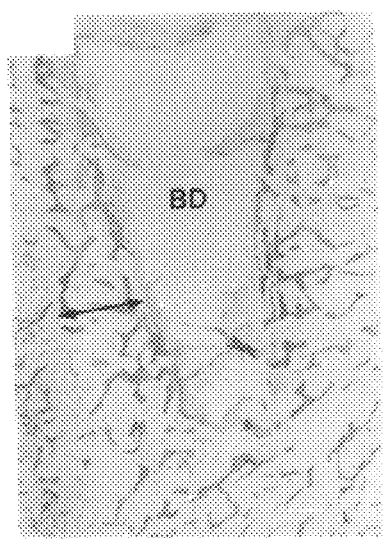
Figure 9D:
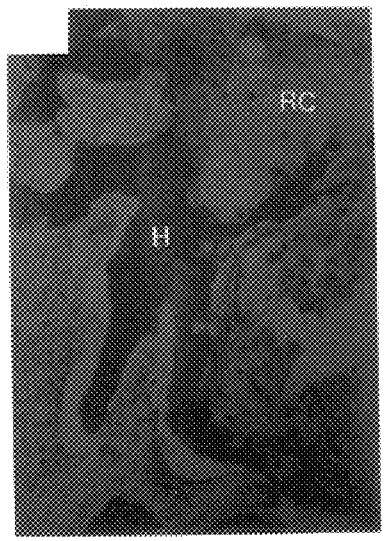
Figure 9E:
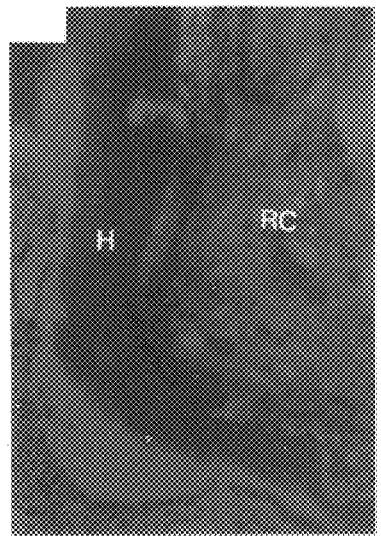
Figure 10A:
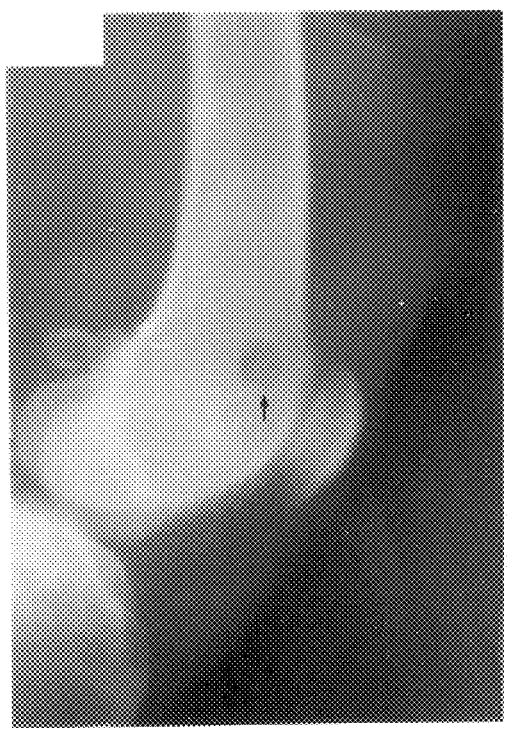
FIG. 10 shows autoradiographs of a thighbone of a beagle dog, which is not treated after a defect is caused in the thighbone, where 10A; just after the operation, 10B; two weeks after the operation, 10C; four weeks after the operation, and 10D; six weeks after the operation.
Figure 10B:
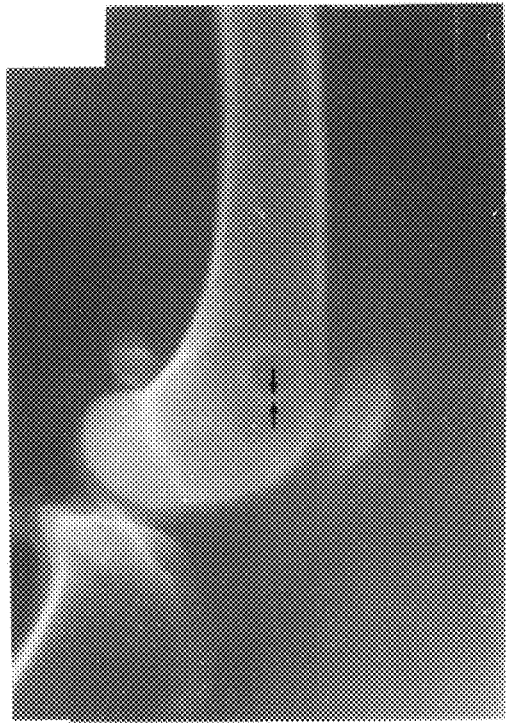
Figure 10C:
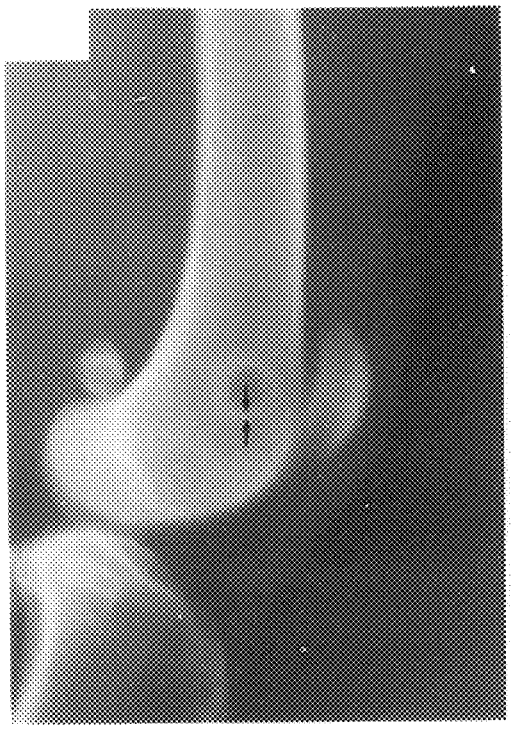
Figure 10D:
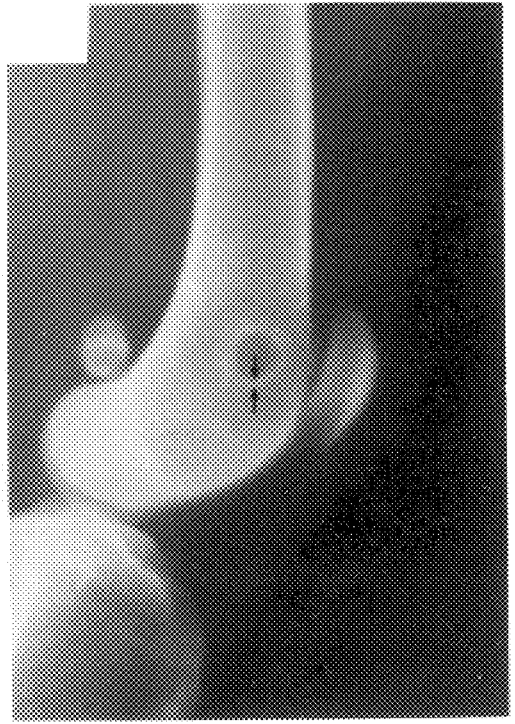
Figure 11A:
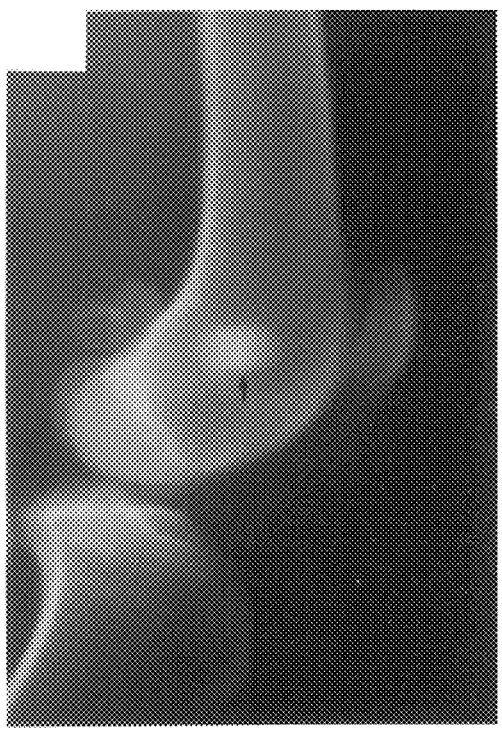
FIG. 11 shows autoradiographs of a thighbone of a beagle dog, into which an artificial bone containing no phosphate is implanted after a defect is caused in the thighbone, where 11A; just after the operation, 11B; two weeks after the operation, 11C; four weeks after the operation, and 11D; six weeks after the operation.
Figure 11B:
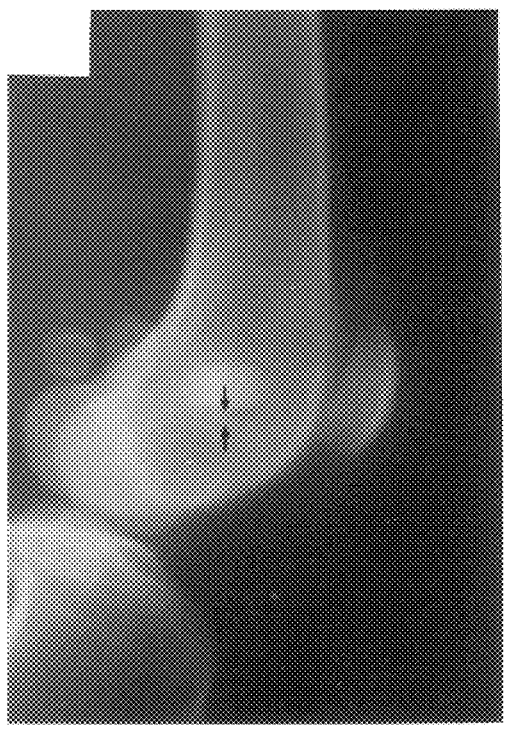
Figure 11C:
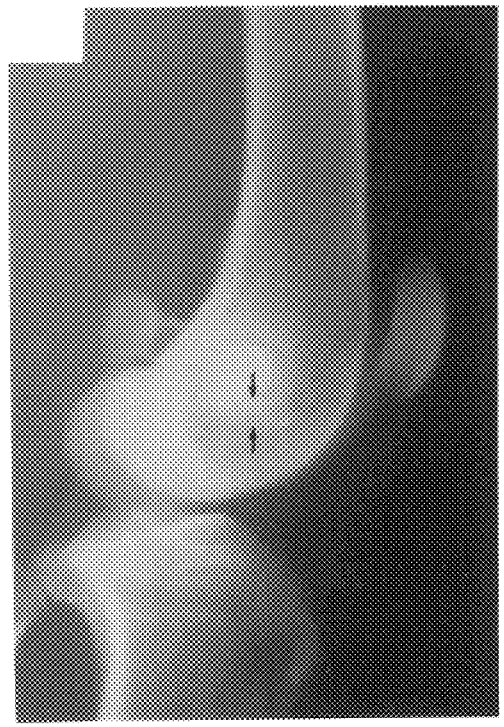
Figure 11D:
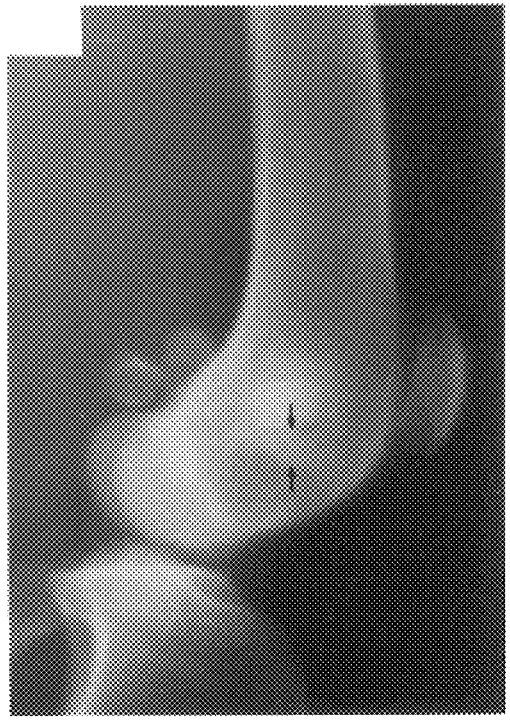
Figure 12A:
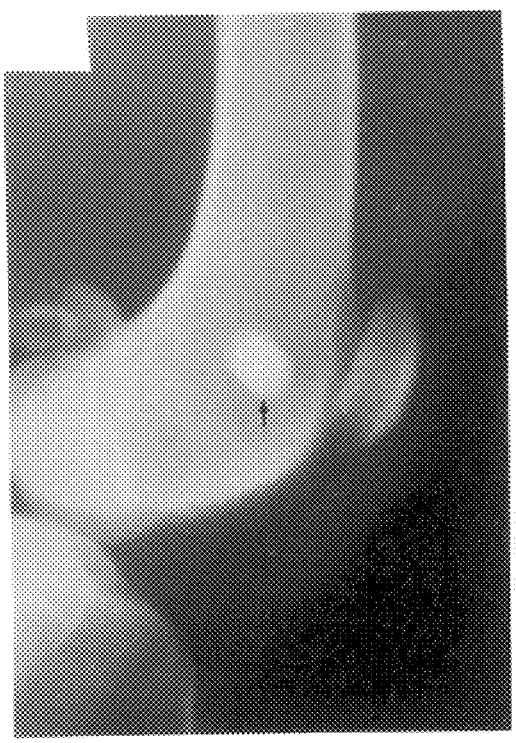
FIG. 12 shows autoradiographs of a thighbone of a beagle dog, into an artificial bone containing 0.01 wt % type 65 polyphosphate is implanted after a defect is caused in the thighbone, where 12A; just after the operation, 12B; two weeks after the operation, 12C; four weeks after the operation, and 12D; six weeks after the operation.
Figure 12B:
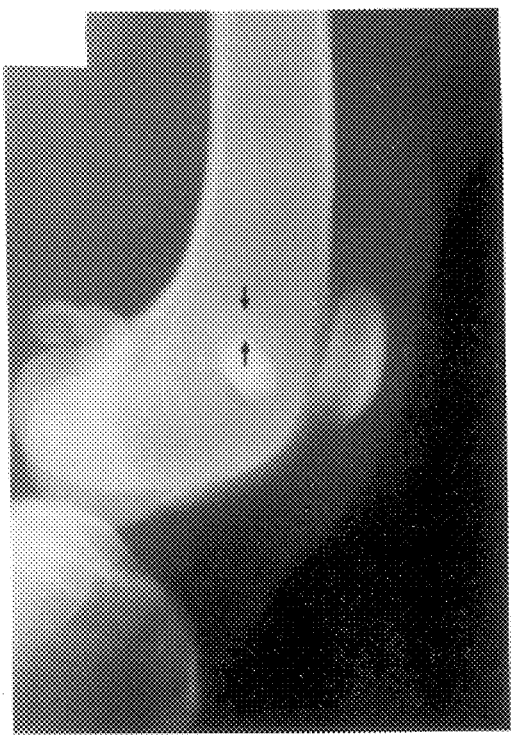
Figure 12C:
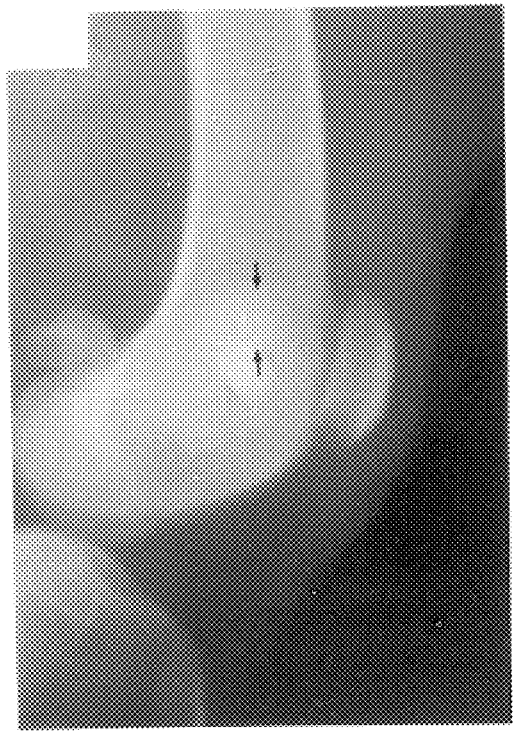
Figure 12D:
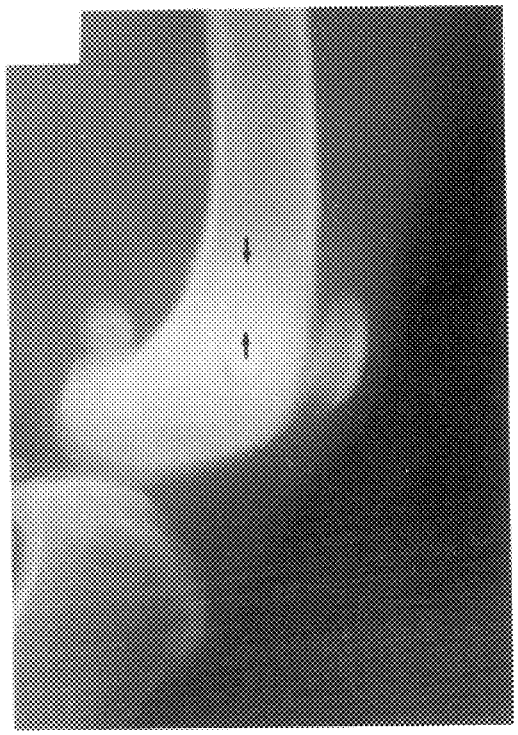

On the other hand, in a tissue specimen of the beagle dog thighbone distal extrerrity, into which the artificial bone cement containing no polyphosphates, instead of the polyphosphate-containing bone cement of the present invention, was transplanted, there was observed that a new bone(N) partially surrounded the bone cement(BC), but osteoclast(indicated by an arrow) was prevalent around the bone cement(BC). Many inflammatory cells were also observed in the interstitial tissue(FIGS. 9c and 9d). In the 100 times magnified, optical microscopic photograph of FIG. 9e, osteoclast(OC) was shown which was gathered around the bone cement(BC).

<3-5> X-Ray Examination

On immediately, two weeks, four weeks, and six weeks after undergoing the surgical operation of causing bone defects and transplanting artificial bones as in Experimental Example <3-3>, the experimental animals were X-rayed to monitor the osteoanagenesis process. For comparison, an experimental animal whose bone defect remained untreated was also employed as a control.

In the experimental animal which was treated with no bone cements, there were found no noticeable differences, except that only a slight increase in bone density at the boundary of the bone defect was observed even six weeks after the operation, as shown in FIG. 10. The experimental animal into which the bone cement with no polyphosphate was transplanted showed that a new bone started to grow in the second week after the operation and grew into a size as large as the transplanted artificial bone after a lapse of six weeks, as shown in FIG. 11. On the other hand, in the experimental animal which was treated with the artificial bone of the present invention, it was found that a new bone started to grow in the second week after the operation and grew into a size 1.5 times as large as the artificial bone after the lapse of six weeks. Therefore, the artificial bone cement supplemented with polyphosphate of the present invention was superior to conventional bone cements in osteoanagenetic potential.

Experimental Example 4

Test for Toxicity of the Polyphosphate-Containing Artificial Bone to the Body

After undergoing the surgical operation of causing bone defects and transplanting artificial bones as in Experimental Example <3-3>, experimental animals were subjected to blood and serologic tests to examine whether the artificial bone grafts show in vivo toxicity or not. For comparison, an animal group whose bone defects remained untreated was employed as a control. While packed cell volume(PCV), hemoglobin density, and total white blood cell number were selected as assay items for the blood tests, measurements were made of total serum proteins, AST, ALT, BUN, creatine, Ca and P for the serologic test.

<4-1> Measurement of the Change in PCV

To measure the change in PCV(packed cell volume) of red blood cells of each experimental groups, every week from just before to six weeks after the operation, blood samples were taken from each experimental animal group. Each blood sample in a tube treated with EDTA, an anticoagulant, was monitored as to the change in packed cell volume with the aid of an automatic QBC hemocytometer(Idexx Co., USA).

Figure 13:
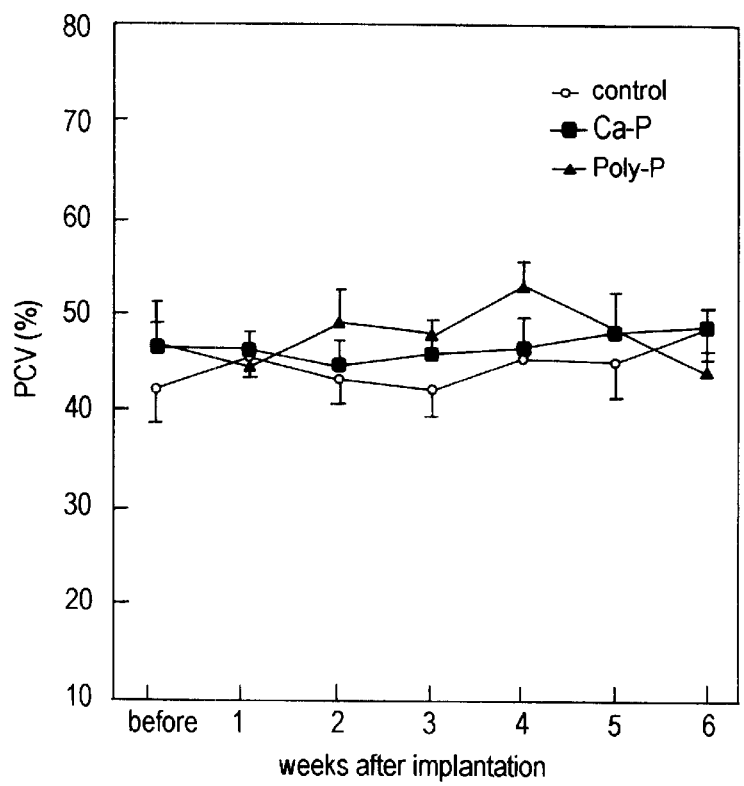
FIG. 13 shows a graph in which PCV levels are plotted with respect to time after the polyphosphate-containing artificial bone of the present invention is transplanted into a thighbone of a beagle dog.

As illustrated in FIG. 13, the PCV of the animal group into which the polyphosphate-containing artificial bone of the present invention was inserted was measured to be within the normal PCV range which is known to be from 35 to 54%(Muir WW and Hubbel JAE, Handbook of veterinary anesthesia, Mosby, St. Louis, p13–15, 1995). Therefore, the polyphosphate-containing artificial bone of the present invention causes no toxicity in terms of the packed cell volume.

<4-2> Measurement of the Change in Hemoglobin Density

Blood samples, which were prepared in a similar manner to that of Experimental Example <4-1>, were measured for the hemoglobin level in blood by use of an automatic QBC hemocytometer(Idexx Co., USA).

Figure 14:
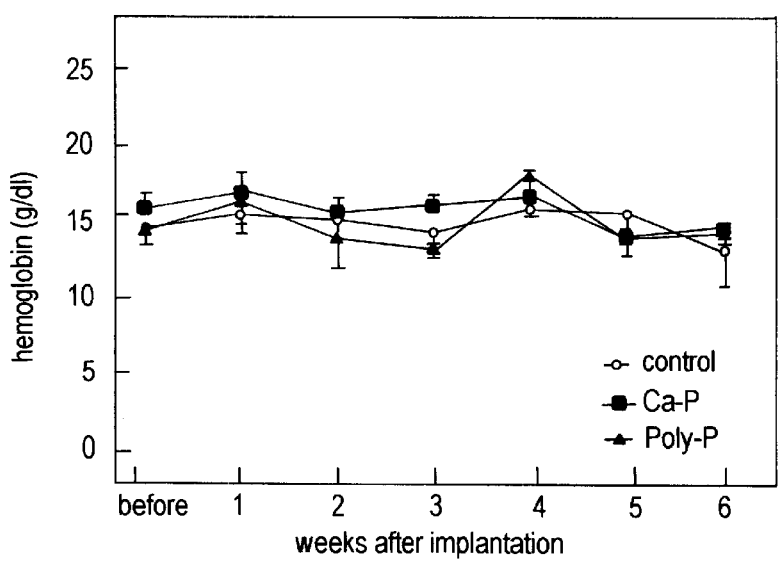
FIG. 14 shows a graph in which hemoglobin concentrations are plotted with respect to time after the polyphosphate-containing artificial bone of the present invention is transplanted into a thighbone of a beagle dog.

During the experiment period, as shown in FIG. 14, the animal group into which the polyphosphate-containing artificial bone of the present invention was inserted was measured to have a normal hemoglobin level in blood, which is known to range from 12.5 to 19 g/dl(Muir WW and Hubbel JAE, Handbook of veterinary anesthesia, Mosby, St. Louis, p13–15, 1995).

Therefore, the polyphosphate-containing artificial bone of the present invention is non-toxic in terms of the hemoglobin level in blood.

<4-3> Measurement of the Change in Total White Blood Cell Number

Blood samples, which were prepared in a similar manner to that of Experimental Example <4-1>, were measured for total white blood cell number by use of an automatic QBC hemocytometer(Idexx Co., USA).

Figure 15:
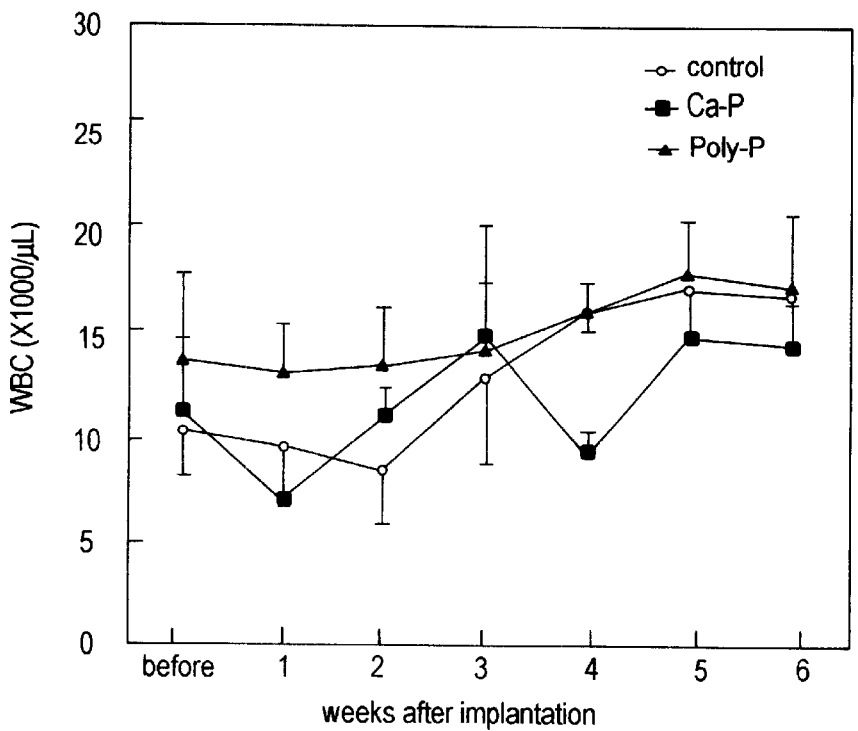
FIG. 15 shows a graph in which white blood cell levels in blood are plotted with respect to time after the polyphosphate-containing artificial bone of the present invention is transplanted into a thighbone of a beagle dog.

As shown in FIG. 15, the animal group into which the polyphosphate-containing artificial bone of the present invention was inserted was measured to range, in total white blood cell number, from 12,920 to 17,667 cells per ml of blood, which is within the normal range which is known to be on the order of 6,500–19,000 cells per ml of blood(Muir WW and Hubbel JAE, Handbook of veterinary anesthesia, Mosby, St. Louis, p13–15, 1995). Therefore, the polyphosphate-containing artificial bone of the present invention causes no negative effects on the total white blood cell number as well as on the immune system of the body.

<4-4> Measurement of the Change in Total Serum Proteins

Blood samples taken as in Experimental Example <4-1> were put in tubes which were not treated with anticoagulants and allowed to be coagulated for 30 min, followed by centrifugation at 3,000 G for 15 min to separate sera. The sera were transferred into sterile tubes and stored at –70° C. until analysis. Using a serum chemical analyzer(Ektachem), the sera were analyzed for concentration changes in total serum proteins.

Figure 16:
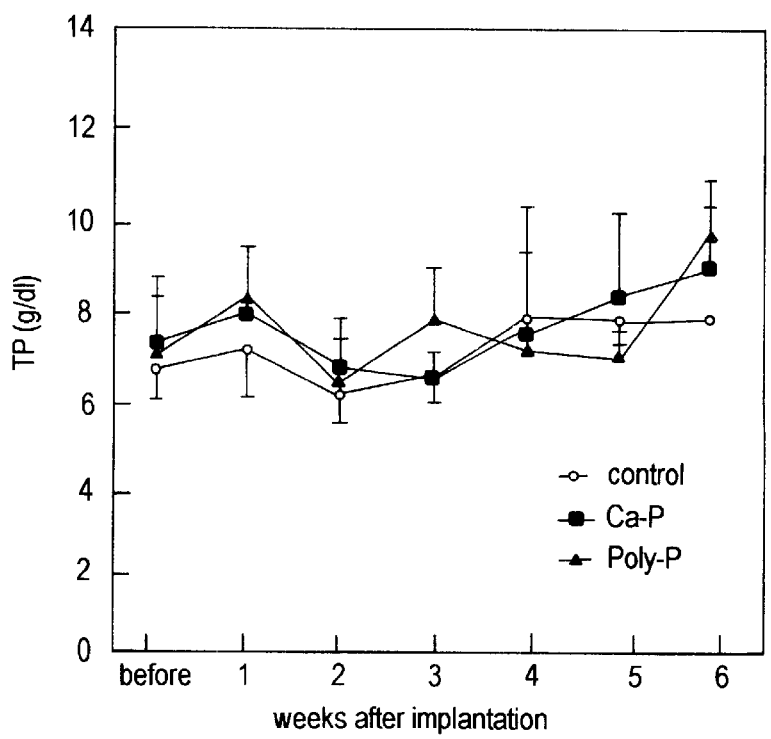
FIG. 16 shows a graph in which total serum protein concentrations are plotted with respect to time after the polyphosphate-containing artificial bone of the present invention is transplanted into a thighbone of a beagle dog.

As illustrated in FIG. 16, the animal group into which the containing-artificial bone of the present invention was inserted was measured to range, in total serum protein, from 6 to 9.4 g/dl, which seems to be somewhat larger than the normal range which is known to be on the order of 6–7.5 g/dl(Muir WW and Hubbel JAE, Handbook of veterinary anesthesia, Mosby, St. Louis, p13–15, 1995), but higher levels than the normal range were observed only on the first and the sixth week after the operation. This inconsistent change is recognized to have nothing to do with the toxicity when account is taken of other assay results.

Therefore, the polyphosphate-containing artificial bone of the present invention has no influence on the total serum protein level in blood.

<4-5> Liver Function Test

To examine the effect which influences the polyphosphate-containing artificial bone of the present invention has on liver functions while existing in vivo to promote osteoanagenesis, sera were assayed for aspartate aminotransferase(AST) and alanine aminotrasferase(ALT). For this, sera, which were prepared in a similar manner to that of Experimental Example <4-4>, were automatically measured for the concentration change in each serum enzyme levels by use of a serum chemical analyzer (Ektachem).

Figure 17:
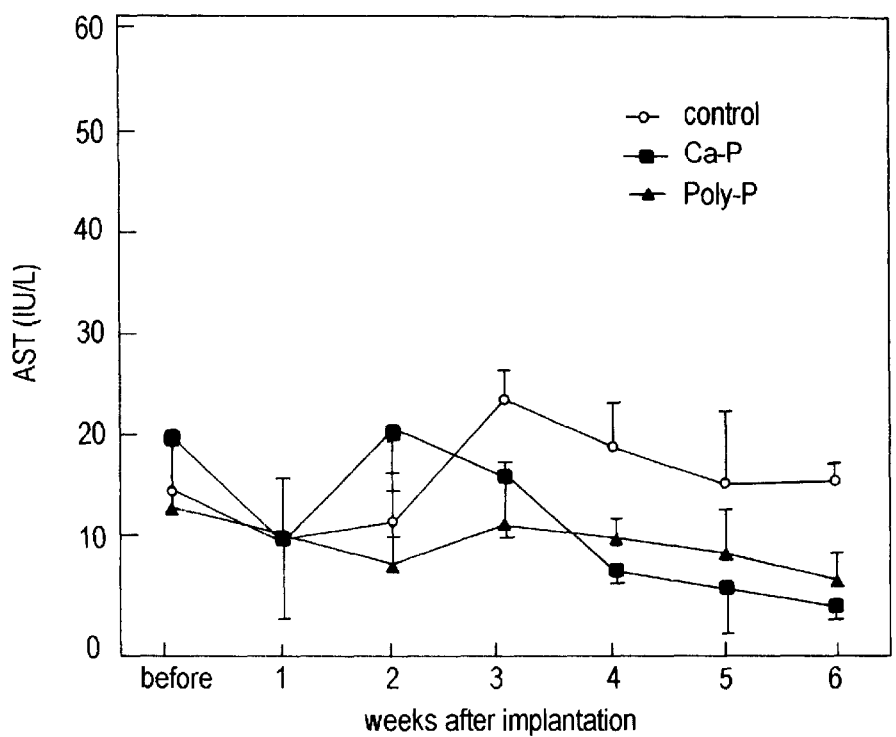
FIG. 17 shows a graph in which white AST concentrations in blood are plotted with respect to time after the polyphosphate-containing artificial bone of the present invention is transplanted into a thighbone of a beagle dog.
Figure 18:
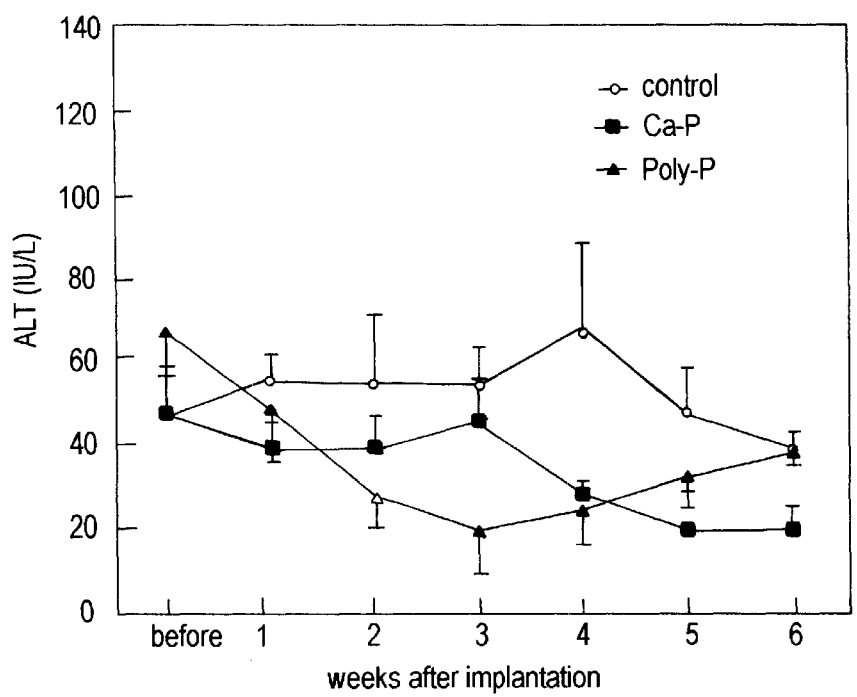
FIG. 18 shows a graph in which ALT concentrations are plotted with respect to time after the polyphosphate-containing artificial bone of the present invention is transplanted into a thighbone of a beagle dog.

As shown in FIGS. 17 and 18, the animal group into which the containing-artificial bone of the present invention was inserted was measured to be not deviated from the normal ranges of AST and ALT levels, which are known to be on the order of 10–50 IU/L and 15–110 IU/L, respectively (Muir WW and Hubbel JAE, Handbook of veterinary anesthesia, Mosby, St. Louis, p13–15, 1995). Therefore, the polyphosphate-containing artificial bone of the present invention causes no toxic effects on the liver function.

<4-6> Kidney Function Test

To examine the effect which influences the polyphosphate-containing artificial bone of the present invention has on kidney functions while existing in vivo to promote osteoanagenesis, sera were prepared in a similar manner to that of Experimental Example <4-4>, and measured for the concentration changes in blood urea nitrogen and creatinine by use of a serum chemical analyzer (Ektachem).

Figure 19:
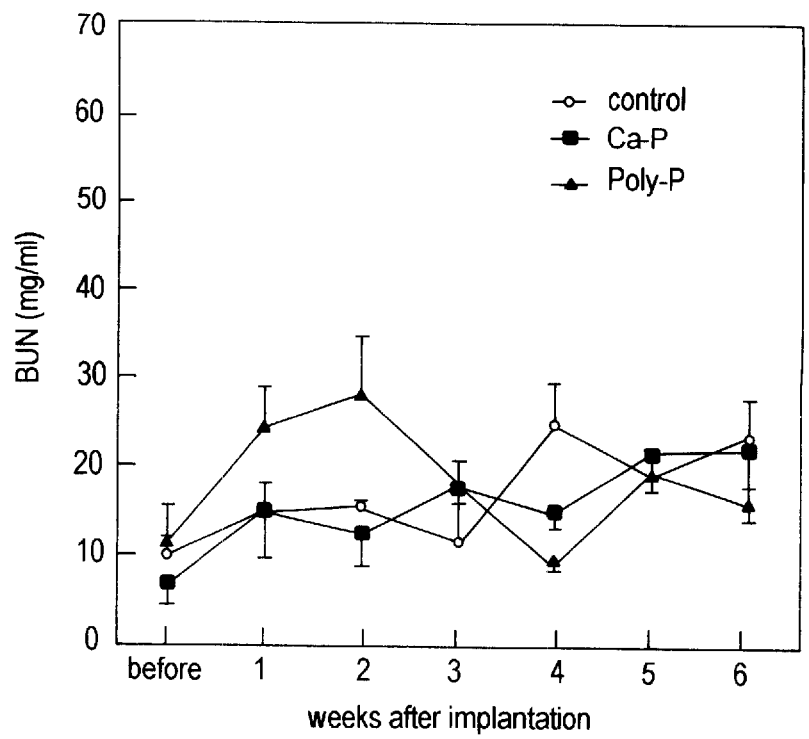
FIG. 19 shows a graph in which urea nitrogen levels in blood are plotted with respect to time after the polyphosphate-containing artificial bone of the present invention is transplanted into a thighbone of a beagle dog.
Figure 20:
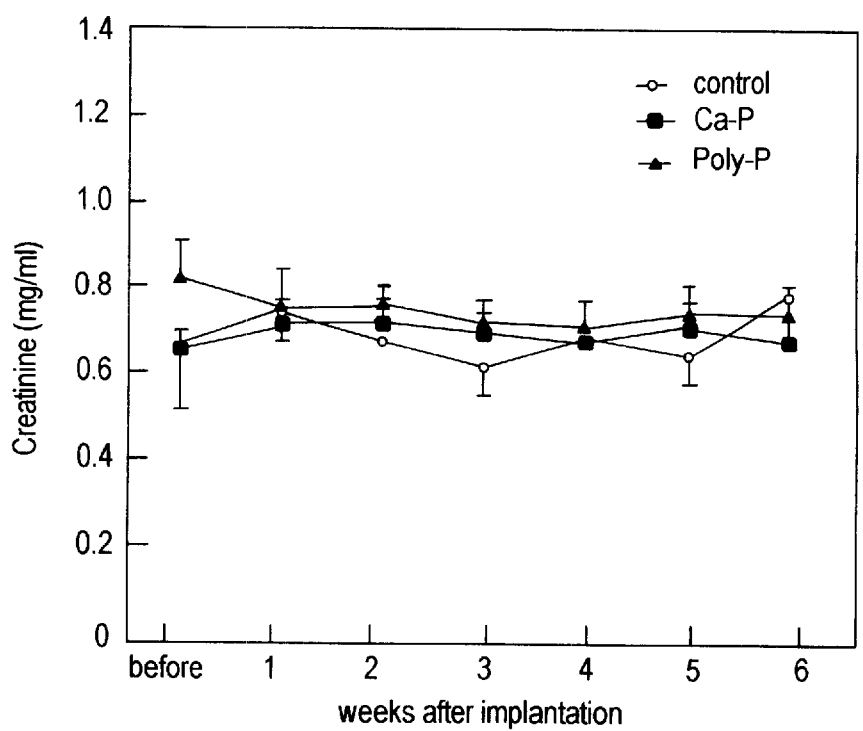
FIG. 20 shows a graph in which creatinine concentrations are plotted with respect to time after the polyphosphate-containing artificial bone of the present invention is transplanted into a thighbone of a beagle dog.

As illustrated in FIGS. 19 and 20, the animal group into which the containing-containing artificial bone of the present invention was inserted was measured to be not deviated from the normal level range of urea nitrogen in blood, which is known to be on the order of 6–30 mg/dl (Muir WW and Hubbel JAE, Handbook of veterinary anesthesia, Mosby, St. Louis, p13–15, 1995). As for the level of creatinine in blood, it was found to be maintained at 0.7–1.3 mg/dl, which is lower than its normal range, indicating that the polyphosphate-containing artificial bone of the present invention causes no toxic effects on the kidney function.

<4-7> Measurement of the Change in calcium and phosphate level in serum

To examine whether the polyphosphate-containing artificial bone of the present invention causes any change in blood calcium and phosphate levels, blood were prepared in a similar manner to that of Experimental Example <4-4>, and monitored for the levels of calcium and phosphate in blood by use of a serum chemical analyzer(Ektachem).

Figure 21:
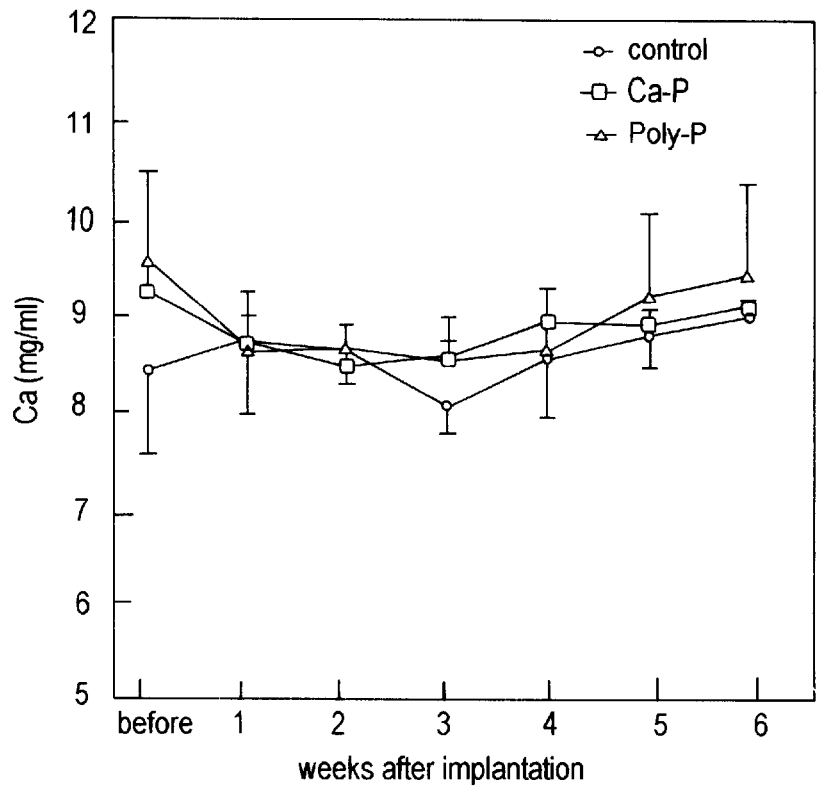
FIG. 21 shows a graph in which calcium levels in blood are plotted with respect to time after the polyphosphate-containing artificial bone of the present invention is transplanted into a thighbone of a beagle dog.
Figure 22:
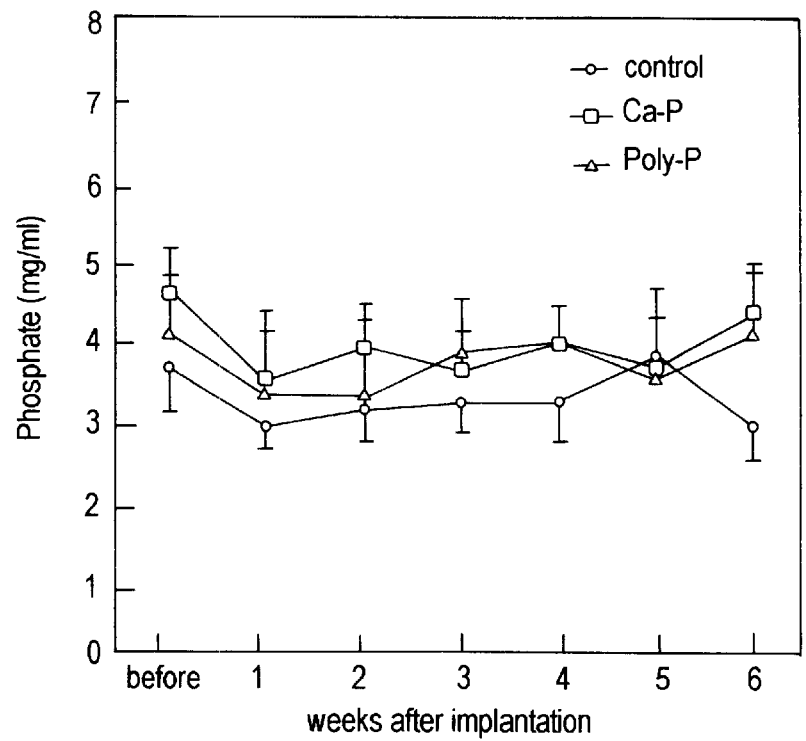
FIG. 22 shows a graph in which phosphate levels in blood are plotted with respect to time after the polyphosphate-containing artificial bone of the present invention is transplanted into a thighbone of a beagle dog.

As illustrated in FIGS. 21 and 22, It was demonstrated that no significant changes were detected in the levels of calcium and phosphate in blood of the experimental animals into which the polyphosphate-containing artificial bone was inserted.

INDUSTRIAL APPLICABILITY

The present invention provides a novel calcium phosphate artificial bone supplemented with linear polyphosphate having excellent biocompatibility, sterilization, osteoinductivity, osteoconductivity, biodegradability and no immunogenicity.

The calcium phosphate artificial bone supplemented with linear polyphosphate of the present invention are useful as substitutes for joints, such as hip joints, knee joints, shoulder joints, and other joints. In addition, the polyphosphate-containing artificial bone of the present invention is safe to the body, chemically stable, and economically favorable in terms of production cost.

Further, the polyphosphate-containing artificial bone of the present invention brings about a reduction in the blood quantity to be transfused during the operation because there are no additional operations to secure bone grafts, or allows the operation to be performed without bleeding. The present invention, thus, can also be applied for patients who are restricted in surgical operations owing to their religious principles.

Those skilled in the art will appreciate that the conceptions and specific embodiments disclosed in the foregoing description may be readily utilized as a basis for modifying or designing other embodiments for carrying out the same purposes of the present invention.

Those skilled in the art will also appreciate that such equivalent embodiments do not depart from the spirit and scope of the invention as set forth in the appended claims.

What is claimed is:

1. A calcium phosphate artificial bone suitable for use in biocompatible bone substitution and osteoanagenesis, comprising a calcium phosphate cement and a polyphosphate, wherein the calcium phosphate cement comprises 50–58 wt. % of β-tricalcium phosphate, 10–15 wt. % of monocalcium phosphate, 8–12 wt. % of calcium sulfate hemihydrate and 5–20 wt. % of other additives.

2. The calcium phosphate artificial bone according to claim 1, which is osteoconductive and osteoinductive, biodegradable substitute material.

3. The calcium phosphate artificial bone according to claim 1, wherein the polyphosphate has a linear structure.

4. The calcium phosphate artificial bone according to claim 1, wherein the polyphosphate is contained in an amount of 0.001 to 0.05% by weight based on the total weight of the artificial bone.

5. The calcium phosphate artificial bone according to claim 1, wherein the chain length of the polyphosphate is 3–200 orthophosphate molecules.

6. The calcium phosphate artificial bone according to claim 1, wherein the chain length of the polyphosphate is 10–100 orthophosphate molecules.

7. The calcium phosphate artificial bone according to claim 1, wherein the chain length of the polyphosphate is 60–80 orthophosphate molecules.

8. The calcium phosphate artificial bone according to claim 1, wherein the polyphosphate is in a salt form.

9. The calcium phosphate artificial bone according to claim 8, wherein the salt form is selected from the group consisting of sodium salt, potassium salt and calcium salt.

10. The calcium phosphate artificial bone according to claim 1, which is applied for the treatment of defects and fractures in every bone of the body, the cure of osteoporous, the fillers of implant for dental surgery, the bone substitute for plastic surgery, the substitution of defected bones in the operation on joints, including hip-joint, knee-joint and shoulder-joint, and the operation on vertabra.

* * * * *